United States Patent
Qian et al.

(10) Patent No.: US 9,139,766 B2
(45) Date of Patent: Sep. 22, 2015

(54) CHEMILUMINESCENT COMPOSITIONS AND ENHANCING REAGENTS FOR CHEMILUMINESCENCE

(71) Applicant: Shenzhen Mindray Bio-Medical Electronics Co., Ltd., Nanshan, Shenzhen (CN)

(72) Inventors: Chungen Qian, Shenzhen (CN); Yuping Zhang, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 215 days.

(21) Appl. No.: 14/051,151

(22) Filed: Oct. 10, 2013

(65) Prior Publication Data

US 2014/0103272 A1    Apr. 17, 2014

Related U.S. Application Data

(62) Division of application No. 13/177,189, filed on Jul. 6, 2011, now Pat. No. 8,563,321.

(30) Foreign Application Priority Data

Jul. 13, 2010    (CN) ........................... 2010 1 0226676

(51) Int. Cl.
*G01N 21/76* (2006.01)
*C09K 11/07* (2006.01)
(Continued)

(52) U.S. Cl.
CPC .............. *C09K 11/07* (2013.01); *G01N 33/532* (2013.01); *G01N 33/542* (2013.01); *G01N 33/58* (2013.01)

(58) Field of Classification Search
None
See application file for complete search history.

(56) References Cited

U.S. PATENT DOCUMENTS 4,857,652 A    8/1989    Schaap
4,959,182 A    9/1990    Schaap
(Continued)

FOREIGN PATENT DOCUMENTS

CN    1719254    1/2006

OTHER PUBLICATIONS

Schaap et al. Clinical Chemistry, vol. 35, No. 9, 1989, pp. 1863-1864.
(Continued)

*Primary Examiner* — Robert Xu
(74) *Attorney, Agent, or Firm* — Kory D. Christensen; Matthew S. Bethards; Stoel Rives LLP

(57) ABSTRACT

An enhancing reagent for enhancing chemiluminescence of 1,2-dioxetane compounds and a method for using the enhancing reagent to enhance the chemiluminescence are provided, in which the enhancing reagent contains an alkyl bis-quaternary ammonium salt of Formula I. A chemiluminescent composition with a 1,2-dioxetane compound as a substrate and a kit thereof are further provided, which contain a 1,2-dioxetane compound and an alkyl bis-quaternary ammonium salt of Formula I.

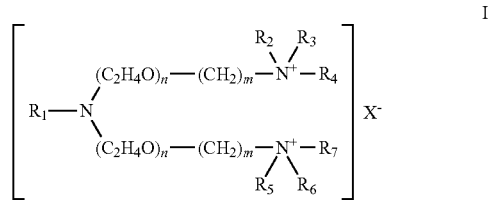

15 Claims, 2 Drawing Sheets

(51) Int. Cl.
  *G01N 33/532* (2006.01)
  *G01N 33/542* (2006.01)
  *G01N 33/58* (2006.01)

(56) References Cited

U.S. PATENT DOCUMENTS

| | | | |
|---|---|---|---|
| 5,004,565 | A | 4/1991 | Schaap |
| 5,145,772 | A | 9/1992 | Voyta et al. |
| 5,393,469 | A | 2/1995 | Akhavan-Tafti |
| 5,547,836 | A | 8/1996 | Bronstein et al. |
| 5,650,099 | A | 7/1997 | Akhavan-Tafti et al. |
| 7,091,051 | B2 | 8/2006 | Kitaoka et al. |
| 8,557,147 | B2 | 10/2013 | Qian et al. |
| 2002/0019553 | A1 | 2/2002 | Akhavan-Tafti et al. |
| 2009/0081696 | A1 | 3/2009 | Sugiyama |

OTHER PUBLICATIONS

Sha et al., 'Progress of Research on Chemiluminescene Enzyme Immunoassay', College of Chemistry, Beijing Normal University, Beijing 100875 China, PTCA (Part B: chem. Anal.) 2010.
Waschinski et al., 'Design of Contact—Active Antimicrobial Acrylate-Based Materials Using Biocidal Macromers.' Advanced Materials, Wiley Interscience, Advanced Materials 20018, 20, pp. 104-108, 2008.
Office Action dated Nov. 2, 2012 for U.S. Appl. No. 13/172,306.
Office Action dated Nov. 6, 2012 for U.S. Appl. No. 13/172,140.
Restriction Requirement dated Aug. 13, 2012 for U.S. Appl. No. 13/172,140.
Restriction Requirement dated Apr. 4, 2013 for U.S. Appl. No. 13/177,189.
Office Action dated Apr. 10, 2013 for U.S. Appl. No. 13/172,306.
Office Action dated May 16, 2013 for U.S. Appl. No. 13/177,189.
Notice of Allowance dated Sep. 9, 2013 for U.S. Appl. No. 13/177,189.

CHEMILUMINESCENT COMPOSITIONS AND ENHANCING REAGENTS FOR CHEMILUMINESCENCE

RELATED APPLICATIONS

This application is a divisional application of U.S. patent application Ser. No. 13/177,189 filed on Jul. 6, 2011, for "CHEMILUMINESCENT COMPOSITIONS, ENHANCING REAGENTS FOR CHEMILUMINESCENCE AND METHODS FOR THE PREPARATION AND USE THEREOF," which claims priority to Chinese Patent Application No. 201010226676.4, filed Jul. 13, 2010, for "ENHANCING REAGENT FOR CHEMILUMINESCENCE, PREPARATION METHOD THEREOF, AND CHEMILUMINESCENT COMPOSITION," each of the disclosures of which are fully incorporated herein by reference.

FIELD OF DISCLOSURE

The present disclosure relates to the field of chemiluminescence immunoassays, particularly reagents and methods for enhancing the chemiluminescence of a 1,2-dioxetane compound, preparation methods and kits thereof, chemiluminescent compositions containing the enhancing reagents, and preparation methods and kits thereof.

DETAILED DESCRIPTION OF THE DISCLOSURE

Figure 1:
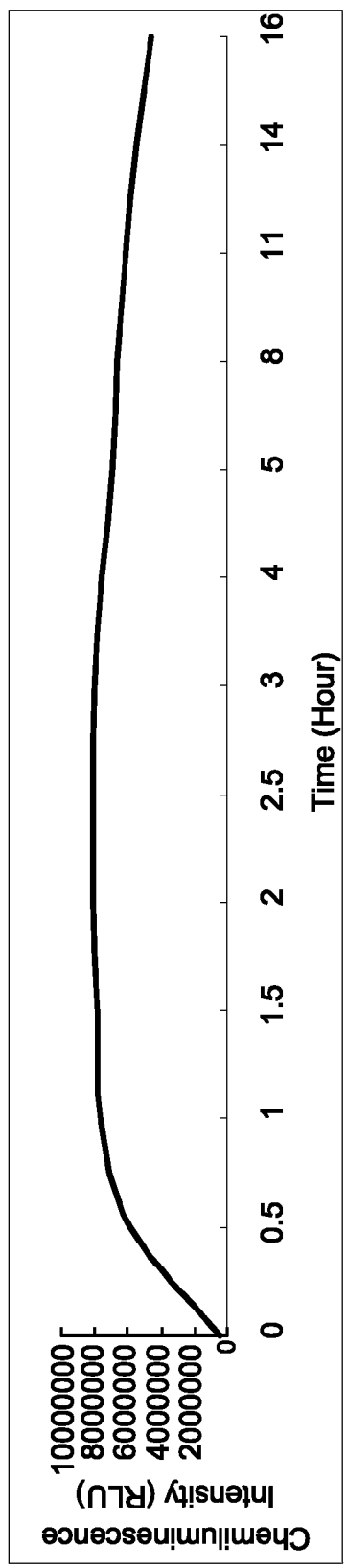
FIG. 1 shows a plot of relative luminescence intensity vs. time for the chemiluminescent composition according to Example 15, wherein the X-axis is time and the Y-axis is relative luminescence intensity.

As a non-radioactive immunoassay technology, chemiluminescence immunoassays developed very quickly in the world after enzyme immunoassay (EIA), radioimmunoassay, and fluorescence immunoassay technologies. Chemiluminescence immunoassay is a microassay technology which has high sensitivity, wide detection range, simple and fast operation, stable label, and low contamination, making it a desirable quantitative immunoassay method.

Luminol, isoluminol, acridine esters, and 1,2-dioxetane compounds are used as luminescent substances in chemiluminescence immunoassays. Isoluminol and acridine esters are labeled directly and act as tracing molecules in flash-type chemiluminescent reactions. However, Luminol and the 1,2-dioxetane compounds are activated by enzymes and act as tracing molecules after enzymatic catalysis in a glow-type chemiluminescent reaction. The 1,2-dioxetane compounds are alkaline phosphatase (ALP) substrates with ultra-high sensitivity. When they contact ALP in appropriate buffers, ALP will hydrolyze them to provide strong optical signals which can be maintained over 20 hours. So, 1,2-dioxetane compounds are regarded as desirable chemiluminescent substances. Several manufacturers have developed kits where ALP is the labeling enzyme and 1,2-dioxetane compounds are ALP's substrates. These kits were used in some automatic chemiluminescence systems, for example, developed by DPC, Beckman, BioMerieux, and Olympus.

Some 1,2-dioxetane compounds such as CSPD, CDP, CDP-Star, and BZPD and luminescent compositions thereof are patented and have good luminescence and high prices. Another 1,2-dioxetane compound, 3-(2-spiroadamantane)-4-methoxy-4-(3-phosphoryloxy)phenyl-1,2-dioxetane (AMPPD), is widely known but the optical signal intensity is much weaker than that of the compounds above.

The molecular structure of AMPPD has a four-member heterocycle with a very weak —O—O— bond and a phosphate group, in which the phosphate group maintains the stability of the whole molecular structure. Normally, this compound is very stable, and is scarcely decomposed when stored at 5° C. as a solid. After catalysis by alkaline phosphatase, AMPPD is hydrolyzed at the phosphate group to form a labile intermediate. The intermediate automatically decomposes, with the four-member heterocycle with an —O—O— bond releasing a great deal of energy, thus exciting a chemiluminescent reaction, and emitting photons.

In 1989, Schaap reported a technology for enhancing the chemiluminescence of 1,2-dioxetane compounds using cetyltrimethylammonium bromide and 5-(N-tetradecanoyl)-aminofluroescein (Clin. Chem., 35). In U.S. Pat. No. 4,959,182 and U.S. Pat. No. 5,004,565, and Chinese Patent CN89106249.1, Schaap describes methods for enhancing chemical and enzymatic triggered chemiluminescence of 1,2-dioxetane compounds by forming a micelle using cetyltrimethylammonium bromide.

U.S. Pat. No. 5,145,772 discloses that poly(vinylbenzyldimethylbenzylammonium chloride) (BDMQ) and a macromolecular substance such as serum albumin can enhance luminescence of 1,2-dioxetane compounds. U.S. Pat. No. 5,547,836 discloses that poly(vinylbenzyltrimethylammonium chloride) (TMQ) and poly(vinylbenzyltributylammonium chloride) (TBQ) are useful as enhancing reagents for luminescence of the 1,2-dioxetane compounds.

U.S. Pat. No. 5,393,469 discloses that polymeric quaternary phosphonium salt provides enhanced chemiluminescence from enzymatically triggered 1,2-dioxetane compounds.

U.S. Pat. No. 5,650,099 and Chinese Patent CN1208399A disclose that dual-cationic surfactants such as trioctylphosphinemethyl-4-tributylphosphinemethylphenyl dichloride, and fluorescent substances such as fluroescein and hydroxypyrenesulfonic acid, provide enhanced luminescence from 1,2-dioxetane compounds.

Chinese Patent CN1719254A discloses a chemiluminescent composition including CSPD as substrate and enhancing reagents containing cetyltrimethylammonium chloride, myristoylglycerol phosphate disodium, bovine serum albumin, and octadecylamino fluroescein.

Most of the enhancing reagents for enhancing luminescence of the 1,2-dioxetane compounds disclosed in the patents above are polymers and long-chain alkyl fluorescent substances, and they are expensive and not easily available.

Therefore, this disclosure provides a new chemiluminescent composition, a new reagent and a method for enhancing the luminescence of 1,2-dioxetane compounds.

The present disclosure relates to enhancing reagents for enhancing chemiluminescence of 1,2-dioxetane compounds, and kits thereof, where the enhancing reagents or the kits contain at least an alkyl bis-quaternary ammonium salt having the structure of General Formula I:

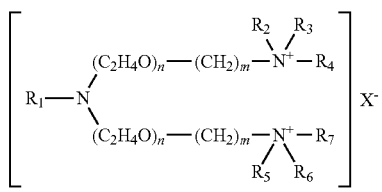

wherein, $R_1$ is selected from at least one of the following: $C_{10-20}$ alkyl, $C_{10-20}$ alkenyl, $C_{10-20}$ alkynyl, and $C_{3-8}$ cycloalkyl$C_{6-12}$ alkyl-; each n is an integer independently selected from 2 to 15, and each m is an integer independently selected from 1 to 6; $R_2$, $R_3$, $R_4$, $R_5$, $R_6$, and $R_7$ are each independently selected from at least one of the following: $C_{1-6}$ alkyl, $C_{2-6}$ alkenyl, $C_{2-6}$ alkynyl, and $C_{3-8}$ cycloalkyl; and $X^-$ is a negative ion.

In a second aspect, the present disclosure relates to methods for preparing enhancing reagents for chemiluminescence of 1,2-dioxetanes, the methods comprising dissolving the components of the enhancing reagents of the present disclosure in water.

In a third aspect, the present disclosure relates to methods for enhancing chemiluminescence of 1,2-dioxetanes, the methods comprising adding the enhancing reagents of the present disclosure to 1,2-dioxetane solutions, or using the kits of the present disclosure.

In a fourth aspect, the present disclosure relates to chemiluminescent compositions and kits thereof, which contain 1,2-dioxetane compounds and the enhancing reagent of the present disclosure.

In a fifth aspect, the present disclosure relates to the use of an alkyl bis-quaternary ammonium salt having a structure of General Formula I in preparing chemiluminescent compositions.

Chemiluminescent enhancing reagents of the present disclosure have simple components and desirable enhancing effects for 1,2-dioxetanes. The chemiluminescent compositions of the present disclosure provide stable, long-lasting and greatly enhanced chemiluminescence signals and may be used in chemiluminescence immunoassays, DNA probe detection, and chemiluminescence analysis of biological membrane protein blotting. The chemiluminescent compositions of the present disclosure may be widely used in the fields of clinical diagnosis, scientific research, environmental and hygiene detection, and forensic identification.

In order to make other aspects and advantages of the present disclosure more apparent, the present disclosure is illustrated with reference to the following description and specific embodiments.

DEFINITIONS

Unless indicated otherwise, terms used herein have the following meanings.

The term "alkyl" as used herein individually or in combination with other groups refers to straight or branched alkyl groups containing 1-18 carbon atoms, such as 1-12, 1-8, and 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules apply to other groups as used throughout the present specification.

The term "alkenyl" refers to a monovalent or divalent hydrocarbon chain having a carbon-carbon double bond, such as a monovalent, unsaturated group having a carbon-carbon double bond. Alkenyl groups may be cyclic, branched, or straight.

The term "alkynyl" refers to a monovalent or divalent unsaturated group containing a carbon-carbon triple bond. Alkynyl groups may be branched or straight.

The term "cycloalkyl" refers to a saturated monocyclic or bicyclic carbocyclic group, such as cyclopropyl, cyclobutyl, cyclopentyl, and cyclohexyl.

The term "aryl" as used herein refers to an optionally substituted aromatic carbocyclic group, such as monocylic or bicylic groups having 6-12 carbon atoms in the ring moiety, for example, phenyl, biphenyl, naphthyl, substituted phenyl, substituted biphenyl, or substituted naphthyl. Preferred aryl groups are phenyl or substituted phenyl.

The term "halogen" as used herein includes fluorine, chlorine, bromine, and iodine.

The term "a soluble salt" as used herein refers to a water soluble salt, and includes, but is not limited to, halide, sulfate, carbonate, and phosphate.

Enhancing Reagent for Chemiluminescence

Chemiluminescence is light generated in a specific reaction of a chemical substance. Singlet molecules are excited and formed as high energy intermediates decompose in a chemical reaction, then the excited singlet molecules return to the ground state, and part of the energy is emitted in the form of luminescence. Therefore, chemiluminescent reactions include two processes: an excitation process and a luminescence process. Some molecular energy will also be dissipated in the excited state because of inter- and intra-system crossing.

The 1,2-dioxetane compounds are chemiluminescent substrates, and their structures are well-known in the art. A typical structure is as follows:

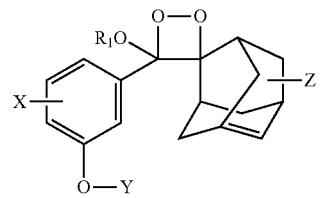

wherein $R_1$ is selected from at least one of alkyl, aryl, aralkyl, alkaryl, heteroalkyl, heteroaryl, cycloalkyl, heterocycloalkyl, alkyloxyalkyl, alkyloxyaryl, alkyloxyhaloalkyl, alkylalkenyl, alkylalkynyl, halogenated alkyl, alkyl alcohol, alkyl carbonitrile, alkyl amine, alkyl acid, halogenated alkyl alcohol, halogenated alkyl carbonitrile, halogenated alkyl amine, and halogenated alkyl acid; X is hydrogen or a substituent on a phenyl ring; Y is hydrogen, alkyl, acetoxyl, t-butyldimethylsilyl, a group capable of being cleaved by an enzyme, or a group capable of being cleaved by an antibody; and Z is hydrogen or a substituent on an adamantane ring.

The 1,2-dioxetane compounds used herein include, but are not limited to, 3-(2'-spiroadamantane)-4-methoxy-4-(3"-phosphoryloxy)phenyl-1,2-dioxetane (AMPPD), disodium 3-(4-methoxyspiro{1,2-dioxetane-3,2'-(5'-chloro)tricyclo[3.3.1.1$^{3,7}$]decan}-4-yl)phenyl phosphate (CSPD), and disodium 2-chloro-5-(4-methoxyspiro{1,2-dioxetane-3,2'-(5'-chloro)-tricyclo[3.3.1.1$^{3,7}$]decan}-4-yl)-1-phenyl phosphate (CDP-Star).

AMPPD can be effectively decomposed by an alkaline phosphatase, by removal of a phosphate group to form an AMPPD intermediate. The intermediate is cleaved into adamantanone and a meta-oxy methyl benzoate anion in the excited state through inter-molecular electron transfer. When the meta-oxy methyl benzoate anion transitions from the excited state to the ground state, light with a maximal wavelength of 477 nm is generated. Chemiluminescence from AMPPD catalyzed with an alkaline phosphatase can reach its peak at 15 min of reaction time, and then the optical signal strength remains relatively constant for between 15 to 60 min, with small variation. Chemiluminescence measurements may still be correct even after 12 h. AMPPD is used in a range of 0.0001-0.01 mol/L.

A person of skill in the art can understand that, based on different cleavable groups, 1,2-dioxetane compounds can be activated using different enzymes, for example, galactosidase, glucose oxidase, and catalase. In addition, Y may be chemically cleaved, to activate the 1,2-dioxetane compounds to emit light.

In chemiluminescence immunoassays, it is expected that chemical bond energy is converted into light energy as efficiently as possible, and that the generated chemiluminescence signal intensity is high and stable. The efficiency of the chemiluminescent reaction is dependent on the quantum efficiency of generating fluorescence and phosphorescence. Methods for improving the chemiluminescence intensity include: improving the quantum yield of luminescent substrate molecules, improving the enzyme activity, and stabilizing the luminescent molecules in the excited state.

In one aspect, the present disclosure provides enhancing reagents for chemiluminescence of 1,2-dioxetanes, and kits thereof, in which the enhancing reagents or the kits contain at least an alkyl bis-quaternary ammonium salt having a structure of General Formula I:

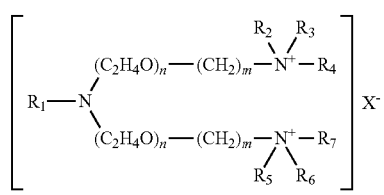

wherein, $R_1$ is selected from at least one of the following: $C_{10-20}$ alkyl, $C_{10-20}$ alkenyl, $C_{10-20}$ alkynyl, and $C_{3-8}$ cycloalkylC$_{6-12}$ alkyl-; each n is an integer independently selected from 2 to 15, and each m is an integer independently selected from 1 to 6; $R_2$, $R_3$, $R_4$, $R_5$, $R_6$, and $R_7$ are each independently selected from at least one of the following: $C_{1-6}$ alkyl, $C_{2-6}$ alkenyl, $C_{2-6}$ alkynyl, and $C_{3-8}$ cycloalkyl; and k is a negative ion.

In another aspect, the present disclosure provides enhancing reagents for chemiluminescence of 1,2-dioxetanes, which contain at least an alkyl bis-quaternary ammonium salt having a structure of General Formula II:

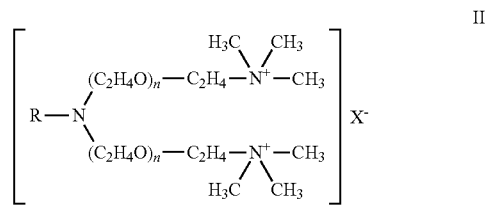

wherein R is selected from $C_{10-20}$ alkyl; each n is an integer independently selected from 5-15; and k is a negative ion.

In one embodiment, $R_2$, $R_3$, $R_4$, $R_5$, $R_6$, and $R_7$ are alkyl, each having the same number of carbon atoms, or are each identical alkyl, or are each independently selected from methyl or ethyl, for example, where the groups are methyl.

In one embodiment, each n is an integer independently selected from 5-10, for example, n may be 5 or 10.

In one embodiment, each m is an integer independently selected from 2 or 3.

In one embodiment, $X^-$ is selected from at least one of the following: halide ions, $ClO_4^-$, $PF_6^-$, $CF_3SO_3^-$, $BF_4^-$, acetate, and p-toluene sulfonate anions.

In one embodiment, R is selected from $C_{12-18}$ alkyl, for example, R may be selected from $C_{12}$ alkyl or $C_{18}$ alkyl.

In one embodiment, the compound is selected from at least one of the following: Compound-1, Compound-2, Compound-3, and Compound-4:

Compound-1: dodecylamino polyoxyethylene ether ammonium dichloride

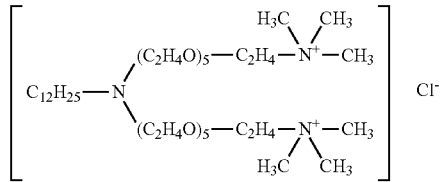

Compound-2: octadecylamino polyoxyethylene ether ammonium dichloride

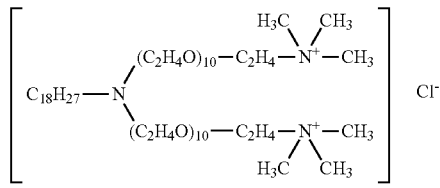

Compound-3: dodecylamino polyoxyethylene ether ammonium dibromide

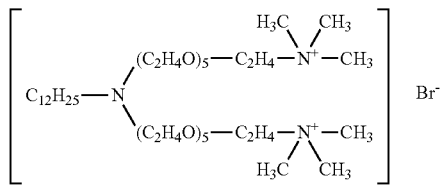

Compound-4: octadecylamino polyoxyethylene ether ammonium dibromide

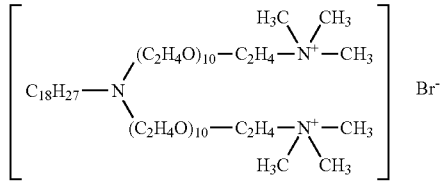

While not being bound by theory, it is believed that the surfactants used in the embodiments of the present disclosure may form micelles in a solution, whose micro environment is non-aqueous. In the non-aqueous environment, the chemiluminescent reaction efficiency and quantum yield improve. Meanwhile, the surfactants may be conducive to the fluorescent molecules moving close to the chemiluminescent substrate molecules, allowing light energy transfer to occur once the chemiluminescence reaction starts. The quantum yield of the fluorescent molecules is much greater than that of the chemiluminescent molecules, thus enhancing the optical signal. The alkyl bis-quaternary ammonium salt is generally used in an amount of 0.1 g/L to 10 g/L, for example, 1 g/L to 10 g/L.

The enhancing reagents according to the embodiments of the present disclosure may further include fluorescent agents, for example, fluorescein sodium, Rhodamine B, and Rhodamine 6G. The fluorescent agents will emit another kind of fluorescence after receiving light energy from the luminescent substance. The quantum yield of fluroescein is far greater than that of the chemiluminescent substance, so the quantum yield of the luminescent substance may indirectly improve. For example, fluorescein sodium (9-(o-carboxyphenyl)-6-hydroxy-3H-xanthene-3-ketone disodium) is a water soluble fluorescent agent, and has an excitation and emission wavelength of 494 nm and 518 nm respectively. The quantum yield of fluorescein sodium is up to 0.97. Similarly, Rhodamine series fluorescent agents also have a very high fluorescence quantum yield. The fluorescent agent is used at concentration of about 0.1 mg/L to about 1 g/L.

Optionally, the enhancing reagents of the present disclosure may further include optional magnesium ions, optional buffers, and optional preservatives, which have the same definitions as the corresponding components in chemiluminescent compositions below.

Components in the enhancing reagents above are dissolved in pure water, and water is added to a final volume, to prepare the enhancing reagents according to the embodiments of the present disclosure.

The enhancing reagents according to the embodiments of the present disclosure may be made into a kit by individually packaging the components of the enhancing reagent to form a multi-package system. Alternatively, the components of the enhancing reagent may be combined according to need, and packaged in a mixture. For example, one package may contain two or more components, and the other packages may individually contain one or more other components. Alternatively, the components may be mixed, and then packaged into a single mixture. The components may be packaged in the form of solution, powder, or lyophilized powder.

Method for Enhancing Chemiluminescence

The present disclosure further provides a method for enhancing luminescence of 1,2-dioxetane compounds, which includes adding the chemiluminescent enhancing reagents of the present disclosure into a solution containing 1,2-dioxetane compounds, or using the kit of the present disclosure.

Chemiluminescent Compositions, and Preparation Method and Kits Thereof

The present disclosure further provides chemiluminescent compositions, which contain 1,2-dioxetane compounds and enhancing reagents of the present disclosure.

The chemiluminescent compositions of the present disclosure may further contain a buffer, for maintaining the pH of the reaction system. The buffer includes a carbonate buffer, a diethanolamine buffer, 2-amino-2-methyl-1-propanol, and so on. When luminescence of a chemiluminescent substance is triggered by cleavage of the phosphate group, an appropriate buffer may be a 2-amino-2-methyl-1-propanol buffer system. For example, in a reaction process where phosphate groups are cleaved by catalysis of alkaline phosphatase, 2-amino-2-methyl-1-propanol may be a phosphate receptor in phosphotransfer, so as to improve the catalytic effect of ALP. As for the alkaline phosphatase system, the most suitable pH for the reaction may range from about 9 to about 10. The buffer may be used at an amount of about 10 to about 500 mM.

The chemiluminescent compositions of the present disclosure may further contain magnesium ions, which are from soluble salts containing magnesium ions, for example, magnesium sulfate, magnesium acetate, magnesium chloride, and other salts from which magnesium ions can be dissociated in solution. When a 1,2-dioxetane compound containing a phosphate group is used as a chemiluminescent substrate, the phosphate group can be hydrolyzed by alkaline phosphatase, thus producing chemiluminescence. In this case, the addition of magnesium ions can activate alkaline phosphatase, thereby improving the catalytic performance of alkaline phosphatase for the hydrolysis reaction. The magnesium ions are used at a concentration range from about 0.001 to about 0.01 mol/L.

The enhancing reagents of the present disclosure may further include a preservative, which facilitates the preservation and long-term storage of the reagent. There is no limitation to the type of the preservative, and commercially available preservatives such as Proclin300, sodium azide, Kathon, and Gentamicin may be used. The preservatives may be used at any concentration which will not influence the chemiluminescent reaction and the activity of alkaline phosphatase.

To obtain the chemiluminescent composition of the present disclosure, the chemiluminescent substrate, such as a 1,2-dioxetane compound, and the enhancing reagent of the present disclosure are mixed and dissolved. Optionally, a buffer component, magnesium ions, or a preservative may be added. According to the conditions required for activating the substrate, the pH of the chemiluminescent composition may be adjusted. For example, if the substrate in the chemiluminescent composition is activated by an alkaline phosphatase, the pH of the enhancing reagent may be adjusted to about 9 to about 10.

The chemiluminescent compositions of the present disclosure may be made into a kit by individually packaging the components of the chemiluminescent composition, or by mixing some of components in one container, while the others are stored in separate containers. Alternatively, the components of the chemiluminescent composition may be formulated as a single mixture. According to different detection uses, the kit may further include corresponding enzyme reagents, labeled enzyme reagent, a solid-phase antibody or a manual which instructs the operator.

Use of Alkyl bis-quaternary Ammonium Salt Having a Structure of Formula I in Preparation of Chemiluminescent Compositions or Enhancing Reagents for Chemiluminescence of 1,2-dioxetane Compounds The present disclosure provides for use of an alkyl bis-quaternary ammonium salt having the structure of General Formula I in preparation of a chemiluminescent composition or enhancing reagent for chemiluminescence using 1,2-dioxetane compounds. The alkyl bis-quaternary ammonium salts of the present disclosure have good chemiluminescent enhancing effects with substances such as 1,2-dioxetane compounds. Moreover, most of these salts are commercially available, inexpensive, and suitable for production of chemiluminescent compositions on a large scale.

EXAMPLES

The present disclosure will be further described with references to the following particular examples. These examples are intended only to be illustrative, but not to limit the scope of the present disclosure in any sense.

Unless otherwise indicated, all of chemical reagents used in the examples were analytic pure, and supplied from Sigma-Aldrich Company. The chemiluminescence analyzer is a BHP9507 chemiluminescence analyzer supplied from Beijing Hamamatsu Photon Techniques Inc.

Examples 1 to 14

A basic luminescent composition was formulated with ultra-pure water as follows:

| | |
|---|---|
| 2-amino-2-methyl-1-propanol | 200 mM |
| AMPPD | 0.5 mM |
| $MgCl_2$ | 5 mM |
| Proclin300 | 0.5 g/L |
| pH was adjusted with HCl | to 9.5 |

Appropriate amounts of components other than AMPPD were weighed, dissolved into ultra-pure water, pH adjusted, and adjusted to final volume with water. AMPPD was then added and dissolved, to obtain the basic luminescent composition in which the final concentrations of the components were as shown in the table above. Components of the respective enhancing reagent were added to the basic luminescent composition to formulate the chemiluminescent compositions of Example 1-14 (see Table 1).

100 μl of the chemiluminescent composition from each example was added to 50 μl of a 1 ng/mL solution of alkaline phosphatase. Chemiluminescence intensity (RLU) was measured by a chemiluminescence analyzer and the fold increase in RLU was calculated for each chemiluminescent composition versus the basic luminescent composition. As shown in examples 2 to 8 of Table 1, the alkyl bis-quaternary ammonium salt used alone enhances chemiluminescence from the chemiluminescent composition; the effect was similar to that of the fluorescent agent used alone. Examples 9 to 14 of Table 1 also show that the alkyl bis-quaternary ammonium salt and the fluorescent agent act synergistically, significantly enhancing the luminescence signal of AMPPD.

TABLE 1

Chemiluminescent compositions of Examples 1-14 and intensity duration of chemiluminescence from AMPPD

| Example | Enhancing component(s) added to basic luminescent composition | Luminescence intensity (RLU) | Fold Increase in RLU |
|---|---|---|---|
| 1 | No | 7070 | 1.0 |
| 2 | 5 mg/L fluorescein Sodium | 53025 | 7.5 |
| 3 | 1 mg/L Rhodamine 6G | 36764 | 5.2 |
| 4 | 10 g/L Compound-1 (dodecylamino polyoxyethylene ether ammonium dichloride) | 38178 | 5.4 |
| 5 | 1 g/L Compound-1 (dodecylamino polyoxyethylene ether ammonium dichloride) | 24038 | 3.4 |
| 6 | 0.1 g/L Compound-1 (dodecylamino polyoxyethylene ether ammonium dichloride) | 14847 | 2.1 |
| 7 | 1 g/L Compound-2 (octadecylamino polyoxyethylene ether ammonium dichloride) | 16968 | 2.4 |
| 8 | 1 g/L Compound-4 (octadecylamino polyoxyethylene ether ammonium dibromide) | 12726 | 1.8 |
| 9 | 5 g/L Compound-1 (dodecylamino polyoxyethylene ether ammonium dichloride), 5 mg/L fluorescein sodium | 1204728 | 170.4 |
| 10 | 10 g/L Compound-1 (dodecylamino polyoxyethylene ether ammonium dichloride), 5 mg/L fluorescein sodium | 1169378 | 165.4 |
| 11 | 0.1 g/L Compound-1 (dodecylamino polyoxyethylene ether ammonium dichloride), 5 mg/L Rhodamine 6G | 873145 | 123.5 |
| 12 | 10 g/L Compound-1 (dodecylamino polyoxyethylene ether ammonium dichloride), 5 mg/L Rhodamine 6G | 1063328 | 150.4 |
| 13 | 5 g/L Compound-2 (octadecylamino polyoxyethylene ether ammonium dichloride), 5 mg/L fluorescein sodium | 674478 | 95.4 |
| 14 | 5 g/L Compound-4 (octadecylamino polyoxyethylene ether ammonium dibromide), 5 mg/L fluorescein sodium | 583275 | 82.5 |

Example 15

Referring to the method of Example 1, a chemiluminescent composition was prepared as follows:

| | |
|---|---|
| 2-amino-2-methyl-1-propanol | 200 mM |
| AMPPD | 0.5 mM |
| $MgCl_2$ | 5 mM |
| Compound-1 (dodecylamino polyoxyethylene ether ammonium dichloride) | 5 g/L |
| Fluorescein Sodium | 5 mg/L |
| Proclin 300 | 0.5 g/L |
| pH was adjusted with HCl | to 9.5 |

100 μl of the chemiluminescent composition was added to 50 μl of a 1 ng/mL solution of alkaline phosphatase. Chemiluminescence intensity was measured by a chemiluminescence analyzer, and a chemiluminescent intensity-time curve was plotted. The results are shown in FIG. 1, which demonstrates that the luminescence signal of the chemiluminescent composition of the present disclosure is stable and long lasting.

Example 16

AMPPD+Enhancing Reagent

Referring to the method of Example 1, chemiluminescent composition was formulated with ultra-pure water as follows:

| | |
|---|---|
| 2-amino-2-methyl-1-propanol | 200 mM |
| AMPPD | 0.5 mM |
| $MgCl_2$ | 5 mM |
| Compound 1 (dodecylamino polyoxyethylene ether ammonium dichloride) | 5 g/L |
| Fluorescein Sodium | 5 mg/L |
| Proclin 300 | 0.5 g/L |
| pH was adjusted with HCl | to 9.5 |

Figure 2:
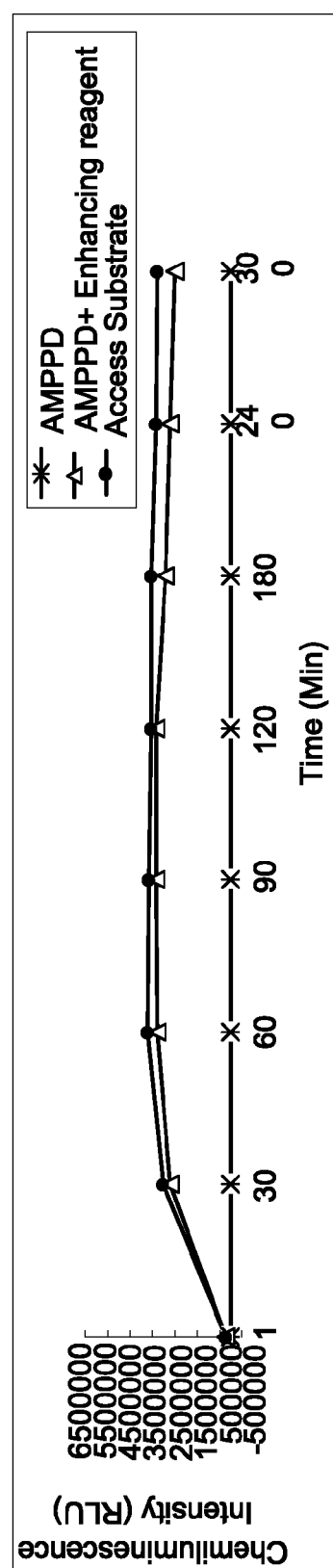
FIG. 2 is a comparison of luminescence signals of luminescent compositions with or without the enhancing reagent in Example 16, with a commercial luminescent composition control, wherein the X-axis is time and the Y-axis is relative luminescence intensity.

100 μl of the chemiluminescent composition was added to 20 μl of a 1 ng/mL solution of alkaline phosphatase. Chemiluminescence intensity was measured by a chemiluminescence analyzer. A commercial chemiluminescent composition, Access Substrate (Beckman), was also measured as a control for comparison. The results are shown in FIG. 2, which demonstrates that the enhancing reagent of the present disclosure enhances the luminescence signal of AMPPD, and that the performance of the chemiluminescent composition is similar to that of Access Substrate (Beckman).

Example 17

CSPD+Enhancing Reagent

Referring to the method of Example 1, a chemiluminescent composition was prepared with ultra-pure water as follows:

| | |
|---|---|
| 2-amino-2-methyl-1-propanol | 200 mM |
| CSPD | 0.25 mM |
| $MgCl_2$ | 5 mM |
| Compound 1 (dodecylamino polyoxyethylene ether ammonium dichloride) | 5 g/L |
| Fluorescein Sodium | 5 mg/L |
| Proclin 300 | 0.5 g/L |
| pH was adjusted with HCl | to 9.5 |

Figure 3:
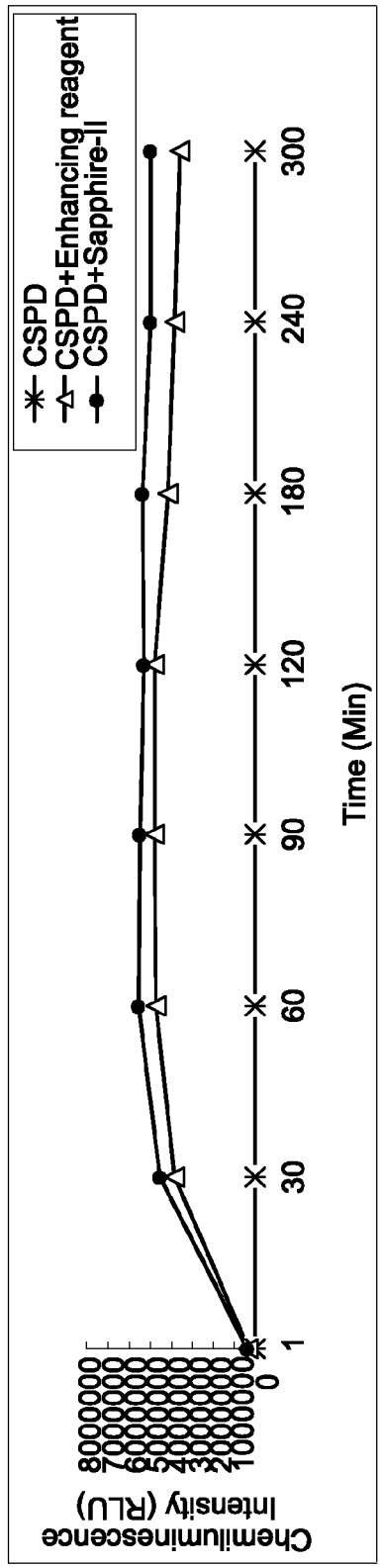
FIG. 3 is a comparison of luminescence signals of luminescent compositions with or without the enhancing reagent in Example 17, with a commercial luminescent composition control, wherein the X-axis is time and the Y-axis is relative luminescence intensity.

100 μl of the chemiluminescent composition was added to 20 μl of a 1 ng/mL solution of alkaline phosphatase. Chemiluminescence intensity was measured by a chemiluminescence analyzer. A commercial chemiluminescent composition, CSPD & Sapphire-II (Tropix), was also measured as a control for comparison. The results are shown in FIG. 3, which demonstrates that the enhancing reagent of the present disclosure enhances the luminescence signal of CSPD, and that the performance of the chemiluminescent composition is similar to that of CSPD & Sapphire-II (Tropix).

Example 18

CDP-Star+Enhancing Reagent

Referring to the method of Example 1, a chemiluminescent composition was prepared with ultra-pure water as follows:

| | |
|---|---|
| 2-amino-2-methyl-1-propanol | 200 mM |
| CDP-Star | 0.25 mM |
| $MgCl_2$ | 5 mM |
| Compound 1 (dodecylamino polyoxyethylene ether ammonium dichloride) | 5 g/L |
| Fluorescein Sodium | 5 mg/L |
| Proclin 300 | 0.5 g/L |
| pH was adjusted with HCl | to 9.5 |

Figure 4:
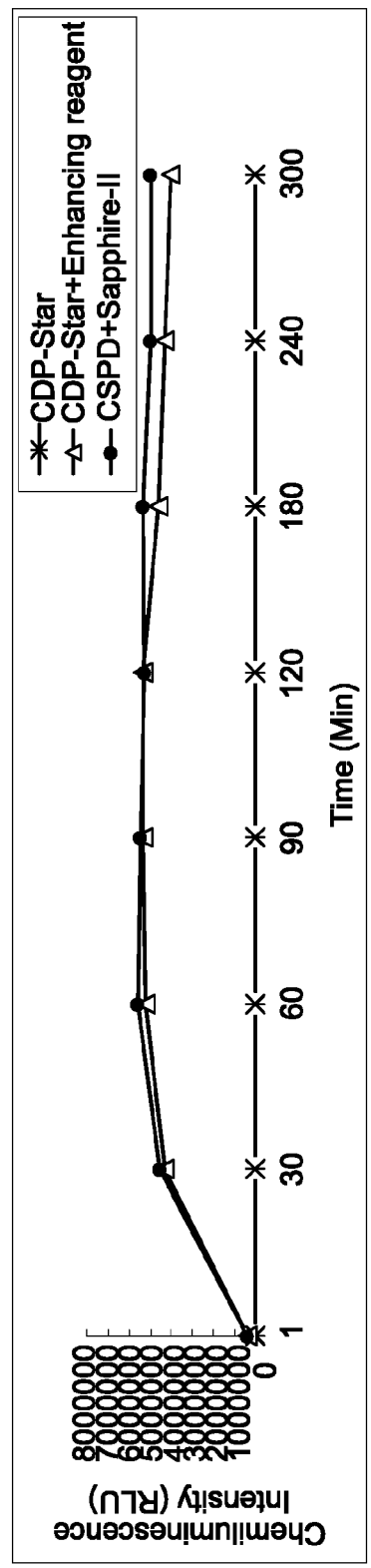
FIG. 4 is a comparison of luminescence signals of luminescent compositions with or without the enhancing reagent in Example 18, with a commercial luminescent composition control, wherein the X-axis is time and the Y-axis is relative luminescence intensity.

100 μl of the chemiluminescent composition was added to 20 μl of a 1 ng/mL solution of alkaline phosphatase. Chemiluminescence intensity was measured by a chemiluminescence analyzer. A commercial chemiluminescent composition, CSPD & Sapphire-II (Tropix), was also measured as a control for comparison. The results are shown in FIG. 4, which demonstrates that the enhancing reagent of the present disclosure enhances the luminescence signal of CDP-Star, and that the performance of the chemiluminescent composition is similar to that of CSPD & Sapphire-II (Tropix).

It can be seen from the examples above that alkyl bis-quaternary ammonium salts demonstrate good chemiluminescent enhancing effects for 1,2-dioxetane compounds, as well as an unexpected synergistic enhancing effects in combination with fluorescent agents. Chemiluminescent compositions containing alkyl bis-quaternary ammonium salts can generate strong luminescence signals, thereby improving the detection sensitivity of a diagnosis kit.

The data, figures, instruments, reagents and steps herein should be understood to be illustrative, but not restrictive. Although the present disclosure was described with references to the above concrete embodiments, many modifications and variances will be apparent to skilled persons in the art. All the modifications and variances also fall within the spirit and scope of the disclosure.

What is claimed is:

1. A chemiluminescent composition comprising a 1,2-dioxetane compound and at least one alkyl bis-quaternary ammonium salt having the structure of General Formula I:

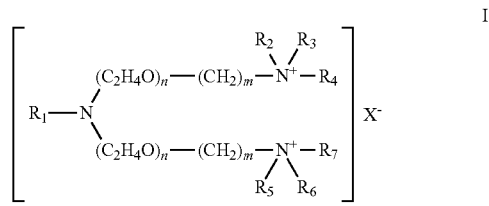

wherein:
R$_1$ is selected from at least one of the following: C$_{10-20}$ alkyl, C$_{10-20}$ alkenyl, C$_{10-20}$ alkynyl, and C$_{3-8}$ cycloalkylC$_{6-12}$ alkyl;
each n is an integer independently selected from 2 to 15;
each m is an integer independently selected from 1 to 6;
R$_2$, R$_3$, R$_4$, R$_5$, R$_6$, and R$_7$ are each independently selected from at least one of the following: C$_{1-6}$ alkyl, C$_{2-6}$ alkenyl, C$_{2-6}$ alkynyl, and C$_{3-8}$ cycloalkyl; and
X$^-$ is a negative ion.

2. The chemiluminescent composition of claim 1, wherein R$_1$ is selected from C$_{12-18}$ alkyl.

3. The chemiluminescent composition of claim 1, wherein R$_2$, R$_3$, R$_4$, R$_5$, R$_6$, and R$_7$ are each independently selected from methyl or ethyl.

4. The chemiluminescent composition of claim 1, wherein R$_2$, R$_3$, R$_4$, R$_5$, R$_6$, and R$_7$ are alkyl, each having the same number of carbon atoms.

5. The chemiluminescent composition of claim 1, wherein each n is an integer independently selected from 5 to 10, or each m is independently selected from 2 or 3.

6. The chemiluminescent composition of claim 1, wherein X$^-$ is selected from at least one of the following: halide ions, $ClO_4^-$, $PF_6^-$, $CF_3SO_3^-$, $BF_4^-$, acetate, and p-toluene sulfonate anions.

7. The chemiluminescent composition of claim 1, wherein the alkyl bis-quaternary ammonium salt compound is selected from at least one of the following: dodecylamino polyoxyethylene ether ammonium dichloride, octadecylamino polyoxyethylene ether ammonium dichloride, dodecylamino polyoxyethylene ether ammonium dibromide, octadecylamino polyoxyethylene ether ammonium dibromide, and a combination thereof.

8. The chemiluminescent composition of claim 1, wherein the concentration of the alkyl bis-quaternary ammonium salt is in a range of between about 0.1 g/L and about 10 g/L.

9. The chemiluminescent composition of claim 1, wherein the concentration of the alkyl bis-quaternary ammonium salt is in a range of between about 1 g/L and about 10 g/L.

10. The chemiluminescent composition of claim 1, further comprising at least one of the following: a fluorescent agent, a magnesium ion, a buffer, and a preservative.

11. The chemiluminescent composition of claim 10, wherein the buffer is 2-amino-2-methyl-1-propanol.

12. A chemiluminescent enhancing reagent configured to enhance the chemiluminescence of a 1,2-dioxetane compound, comprising:

at least one alkyl bis-quaternary ammonium salt having the structure of General Formula I:

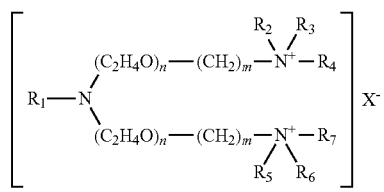

wherein:
$R_1$ is selected from at least one of the following: $C_{10-20}$ alkyl, $C_{10-20}$ alkenyl, $C_{10-20}$ alkynyl, and $C_{3-8}$ cycloalkyl$C_{6-12}$ alkyl;
each n is an integer independently selected from 2 to 15;
each m is an integer independently selected from 1 to 6;
$R_2$, $R_3$, $R_4$, $R_5$, $R_6$, and $R_7$ are each independently selected from at least one of the following: $C_{1-6}$ alkyl, $C_{2-6}$ alkenyl, $C_{2-6}$ alkynyl, and $C_{3-8}$ cycloalkyl; and
$X^-$ is a negative ion; and
a solvent configured to dissolve the alkyl bis-quaternary ammonium salt and the 1,2-dioxetane compound.

13. The chemiluminescent enhancing reagent of claim 12, wherein the enhancing reagent further comprises at least one of the following: a fluorescent agent, a magnesium ion, a buffer, and a preservative.

14. A kit for enhancing the chemiluminescence of 1,2-dioxetane compounds, comprising: at least one alkyl bis-quaternary ammonium salt having the structure of General Formula I:

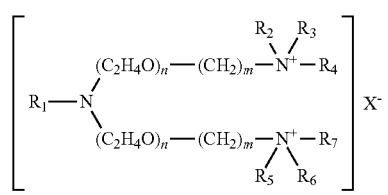

wherein:
$R_1$ is selected from at least one of the following: $C_{10-20}$ alkyl, $C_{10-20}$ alkenyl, $C_{10-20}$ alkynyl, and $C_{3-8}$ cycloalkyl$C_{6-12}$ alkyl;
each n is an integer independently selected from 2 to 15;
each m is an integer independently selected from 1 to 6;
$R_2$, $R_3$, $R_4$, $R_5$, $R_6$, and $R_7$ are each independently selected from at least one of the following: $C_{1-6}$ alkyl, $C_{2-6}$ alkenyl, $C_{2-6}$ alkynyl, and $C_{3-8}$ cycloalkyl; and
$X^-$ is a negative ion; and
a manual instructing the user to mix the alkyl bis-quaternary ammonium salt with the 1,2-dioxetane compound.

15. The kit of claim 14, wherein the components of the kit are stored individually or in the form of one or more mixtures.

* * * * *